US008821805B2

(12) United States Patent
Luo et al.

(10) Patent No.: US 8,821,805 B2
(45) Date of Patent: Sep. 2, 2014

(54) PROCESS UNIT WITH IMPROVED REACTANT FEEDING FOR THE PRODUCTION OF ALKYLATE GASOLINE (75) Inventors: Huping Luo, Richmond, CA (US); Moinuddin Ahmed, Hercules, CA (US); Krishniah Parimi, Alamo, CA (US); Bong-Kyu Chang, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/611,937

(22) Filed: Sep. 12, 2012

(65) Prior Publication Data
US 2013/0004378 A1    Jan. 3, 2013

Related U.S. Application Data (62) Division of application No. 12/780,452, filed on May 14, 2010.

(51) Int. Cl.
| B01J 19/24 | (2006.01) |
| B01J 19/26 | (2006.01) |
| C10L 1/06 | (2006.01) |
| B01J 4/00 | (2006.01) |
| C07C 2/60 | (2006.01) |
| C10G 29/20 | (2006.01) |

(52) U.S. Cl.
CPC .............. *B01J 19/2465* (2013.01); *C10L 1/06* (2013.01); *B01J 4/002* (2013.01); *C07C 2/60* (2013.01); *C10G 2300/305* (2013.01); *C10G 29/205* (2013.01); *C07C 2531/02* (2013.01); *B01J 19/26* (2013.01); *C10G 2400/02* (2013.01); *C07C 2527/125* (2013.01); *C10G 2300/1088* (2013.01)
USPC ........... 422/234; 422/224; 239/398; 239/400; 239/427.3

(58) Field of Classification Search
CPC ........ B01J 4/002; B01J 19/2465; B01J 19/26; C07C 2/60; C10G 2300/305
USPC ................ 422/234, 224; 239/398, 400, 427.3
See application file for complete search history.

(56) References Cited

U.S. PATENT DOCUMENTS

| 3,696,168 | A | * | 10/1972 | Vanderveen | .................. 585/720 |
| 3,758,613 | A | | 9/1973 | Anderson | |
| 3,847,375 | A | * | 11/1974 | Kuerten et al. | ............... 366/101 |
| 3,867,103 | A | * | 2/1975 | Boney et al. | .................. 422/606 |
| 4,294,800 | A | | 10/1981 | Tavlarides et al. | |
| 4,383,977 | A | | 5/1983 | Hutson et al. | |
| 5,443,799 | A | | 8/1995 | Alexanyan et al. | |
| 5,534,657 | A | | 7/1996 | Randolph et al. | |
| 5,583,275 | A | | 12/1996 | Kranz et al. | |
| 6,455,015 | B1 | | 9/2002 | Kilroy | |
| 7,432,408 | B2 | | 10/2008 | Timken et al. | |
| 7,432,409 | B2 | | 10/2008 | Elomari et al. | |
| 7,495,144 | B2 | | 2/2009 | Elomari | |
| 7,553,999 | B2 | | 6/2009 | Elomari et al. | |

(Continued)

*Primary Examiner* — Lessanework Seifu
(74) *Attorney, Agent, or Firm* — Susan M. Abernathy (57) ABSTRACT

This application provides a process unit for the production of alkylate gasoline, comprising: a) a nozzle having an orifice that dispenses one or more recirculated streams comprising ionic liquid catalyst into a chamber in the nozzle, b) a conduit for introducing a hydrocarbon feed stream comprising an olefin to the orifice at a close distance from the orifice; and c) a throat connecting the chamber in the nozzle to an alkylation zone. The process unit can have multiple Venturi nozzles.

13 Claims, 6 Drawing Sheets

(56) References Cited

U.S. PATENT DOCUMENTS

| | | |
|---|---|---|
| 7,651,970 B2 | 1/2010 | Elomari et al. |
| 7,666,811 B2 | 2/2010 | Elomari et al. |
| 7,674,739 B2 | 3/2010 | Elomari et al. |
| 7,678,727 B2 | 3/2010 | Harris et al. |
| 7,691,771 B2 | 4/2010 | Harris et al. |
| 2007/0142211 A1 | 6/2007 | Elomari et al. |
| 2007/0142213 A1 | 6/2007 | Elomari et al. |
| 2007/0142216 A1 | 6/2007 | Harris et al. |
| 2007/0142217 A1 | 6/2007 | Elomari et al. |
| 2009/0163349 A1 | 6/2009 | Elomari et al. |
| 2009/0166257 A1 | 7/2009 | Luo et al. |
| 2009/0170687 A1 | 7/2009 | Luo et al. |
| 2009/0170688 A1 | 7/2009 | Chang et al. |
| 2009/0171133 A1 | 7/2009 | Luo et al. |
| 2009/0171134 A1 | 7/2009 | Luo et al. |
| 2009/0253572 A1 | 10/2009 | Elomari et al. |

\* cited by examiner

PROCESS UNIT WITH IMPROVED REACTANT FEEDING FOR THE PRODUCTION OF ALKYLATE GASOLINE

This application is a division to prior U.S. application Ser. No. 12/780,452, filed on May 14, 2010, published as US20110282114A1, in Group Art Unit 1772; and herein incorporated in its entirety.

TECHNICAL FIELD

This application is directed to a method of feeding reactants in a process for the production of alkylate gasoline blending components and to a process unit for the production of alkylate gasoline blending components.

SUMMARY

This application provides a process for the production of alkylate blending components, comprising introducing a hydrocarbon feed stream comprising an olefin to an orifice of a nozzle, at a distance from the orifice that is within 25 times a diameter of the orifice; and wherein the nozzle dispenses a mixture of one or more recirculated streams and the hydrocarbon feed stream through a throat of the nozzle to make alkylate gasoline blending components.

This application also provides a process unit for the production of alkylate gasoline, comprising:
a) a nozzle having an orifice that dispenses one or more recirculated streams comprising ionic liquid catalyst into a chamber in the nozzle,
b) a conduit for introducing a hydrocarbon feed stream comprising an olefin to the orifice at a distance from the orifice that is within 25 times a diameter of the orifice; and
c) a throat connecting the chamber in the nozzle to an alkylation zone where alkylate gasoline blending components are produced.

DETAILED DESCRIPTION

Examples of alkylation processes for the production of high quality gasoline blending components are taught in U.S. Pat. Nos. 7,432,408, 7,432,409, 7,495,144, 7,553,999; and US Patent Application Publications 2009/0171134, 2009/0171133, and 2009/0166257. The hydrocarbon feed stream comprises an olefin. In some embodiment the hydrocarbon feed stream additionally comprises an isoparaffin. Olefin means any unsaturated hydrocarbon compound having at least one carbon-to-carbon double bond. Examples of olefins are ethylene, propylene, butylene, and pentene. Isoparaffin means any branched-chain saturated hydrocarbon compound. Examples of isoparaffins include isobutane, isopentane, and mixtures thereof. The olefins and isoparaffins can come from any source, including varied refinery streams or from Fischer-Tropsch processes. The hydrocarbon feed stream can comprise a mixture of olefins, a mixture of isoparaffins, and combinations thereof.

The nozzle dispenses a mixture of one or more recirculated streams and the hydrocarbon feed stream via an orifice through a throat of the nozzle. The mixture comprises an isoparaffin, that is supplied from either the hydrocarbon feed stream, the one or more recirculated streams, or both. The orifice of the nozzle is positioned towards one end of the nozzle, at the end from which the nozzle dispenses the mixture of one or more recirculated streams and the hydrocarbon feed stream. The orifice has a diameter that is designed to provide optimal linear velocity and mixing of the components of the mixture. The diameter of the orifice of the nozzle is sized to match the volume of the mixture being dispensed.

The one or more recirculated streams can comprise a catalyst. The one or more recirculated streams can also comprise un-reacted reactants, e.g. one or more isoparaffins. In one embodiment the one or more recirculated streams are recirculated from a reaction zone. An internal recirculated stream is one that feeds directly from a reaction zone. An external recirculated stream is one that feeds indirectly from the reaction zone. In one embodiment, the one or more recirculated streams comprise an external recirculated stream, an internal recirculated stream, and mixtures thereof. In one embodiment, the hydrocarbon feed stream is introduced to a chamber of the nozzle housing a center piece from which the external recirculated stream flows towards the orifice. This embodiment is illustrated in the figures. In one embodiment the one or more recirculated streams come from an alkylation zone comprising an ionic liquid catalyst. In another embodiment the mixture of the recirculated streams and the hydrocarbon feed stream are dispensed through a throat of the nozzle into an alkylation zone comprising an ionic liquid catalyst.

In one embodiment the external recirculated stream comprises regenerated acidic ionic liquid catalyst. The regenerated acidic ionic liquid catalyst can comprise conjunct polymers at a lower level than the amount of conjunct polymers in un-regenerated acidic ionic liquid catalyst. Processes for regenerating acidic ionic liquid catalysts are described in U.S. Pat. Nos. 7,666,811, 7,691,771, 7,651,970, 7,678,727, 7,674,739; and US Patent Application Publication Numbers 2007/0142217, 2007/0142213, 2007/0142211, 2007/0142216, 2009/0253572, 2009/0163349, 2009/0170687, and 2009/0170688.

Figure 6A:
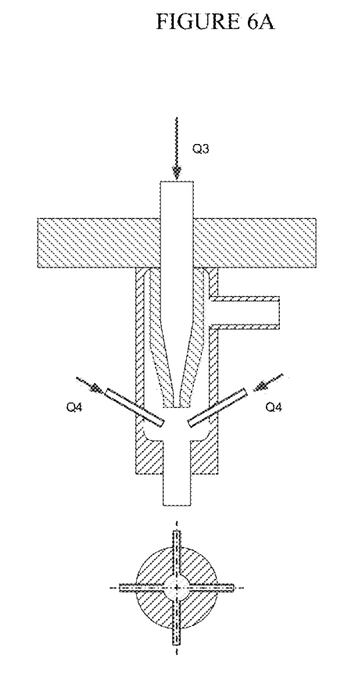
FIG. 6A is a Venturi nozzle with the location of the introduction of the four hydrocarbon feed streams in the chamber of the nozzle, in between the orifice and the throat of the nozzle.
Figure 6B:
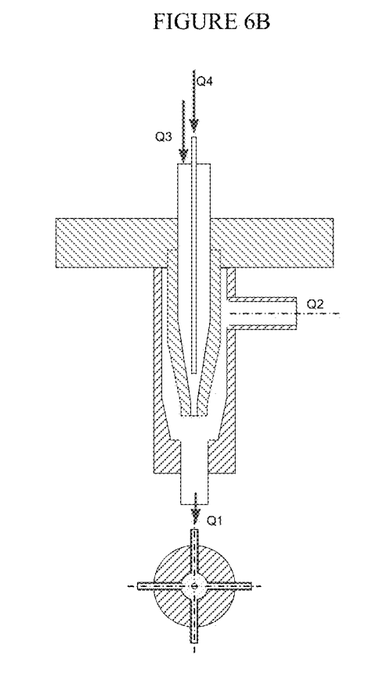
FIG. 6B is a Venturi nozzle loop reactor where the hydrocarbon feed stream (Q4) is introduced through a dip tube into the center piece of the nozzle (rather than into the chamber or the throat of the nozzle).

In one embodiment the hydrocarbon feed stream is introduced at an angle from 0 degrees to 90 degrees from a direction of a flow of the one or more recirculated streams towards the orifice. For example the angle can be from 0 to 10 degrees, from 35 degrees to 75 degrees, or from about 45 degrees to about 65 degrees. The angle can be selected to give the optimal mixing of the recirculated streams and the hydrocarbon feed stream and to make the desired quality alkylate gasoline blending components. One example is where the hydrocarbon feed stream is introduced through a dip tube into an external recirculated stream in a center piece of the nozzle prior to dispensing the mixture of one or more recirculated streams and the hydrocarbon feed stream through the throat of the nozzle. One embodiment of this is illustrated in FIG. 6B.

In one embodiment the nozzle dispenses the mixture of the recirculated streams and the hydrocarbon feed stream through the throat of the nozzle into an alkylation zone comprising an ionic liquid catalyst. An alkylation zone is a zone comprising at least one isoparaffin and at least one olefin, in which the isoparaffin and olefin are alkylated under alkylation conditions. Examples of alkylation zones are reactors and reactor vessels. Alkylation conditions are produced in the alkylation zone. For example, the molar ratio between the olefin and the isoparaffin can be in the range of 1 to 100, 2 to 50, 2 to 20, or 2 to 10. Catalyst volume in the alkylation zone can be in the range of 2 vol % to 70 vol %, or 5 vol % to 50 vol %. The temperature in the alkylation zone can be in the range of −20° C. to 100° C. The pressure in the alkylation zone can be in the range of atmospheric pressure to 8000 kPa. Alternatively, the pressure can be any pressure sufficient to keep the reactants in the mixture dispensed from the nozzle in the liquid phase. The residence time of the reactants in the alkylation zone can be in the range of 0.01 seconds to 60 minutes. In one embodiment the residence time of the reactants in the alkylation zone is less than 3 seconds, less than 2 seconds, from 0.05 to 1 second, or from 0.02 to 0.5 second. One advantage of introducing the hydrocarbon feed stream close to the orifice of the nozzle is that it shortens the residence time of the reactants in the zone where there is insufficient mixing.

In one embodiment, the nozzle provides sufficient mixing and excellent interfacial contact between the hydrocarbon feed stream and the catalyst in the recirculated streams, such that the process provides high quality gasoline blending components. In one embodiment, the nozzle has dimensions compatible to the feed liquid rates to obtain relatively a small droplet size of the catalyst to maximizing interfacial surface area.

The hydrocarbon feed stream is introduced to the orifice of the nozzle at a distance close to the orifice. The positioning of the introduction location close to the orifice improves the alkylate product selectivity. Generally, the distance is within 25 times the diameter of the orifice of the nozzle. In some embodiments the distance maybe from zero to 25 times the diameter, or zero to 10 times the diameter, or zero to 5 times the diameter, or zero to 2 times the diameter. In one embodiment, the positioning of the introduction location is directly adjacent to the orifice.

One advantage to positioning the introduction location of the hydrocarbon feed stream close to the orifice of the nozzle is that it can reduce an undesired production of high boiling products that comprise C11+ hydrocarbons. The production of C11+ hydrocarbons can be reduced to less than 10 wt %, less than 8 wt %, less than 6 wt %, less than 4.8 wt %, less than 4.6 wt %, less than 4 wt %, or even less than 3.5 wt % C11+ hydrocarbons.

Figure 1:
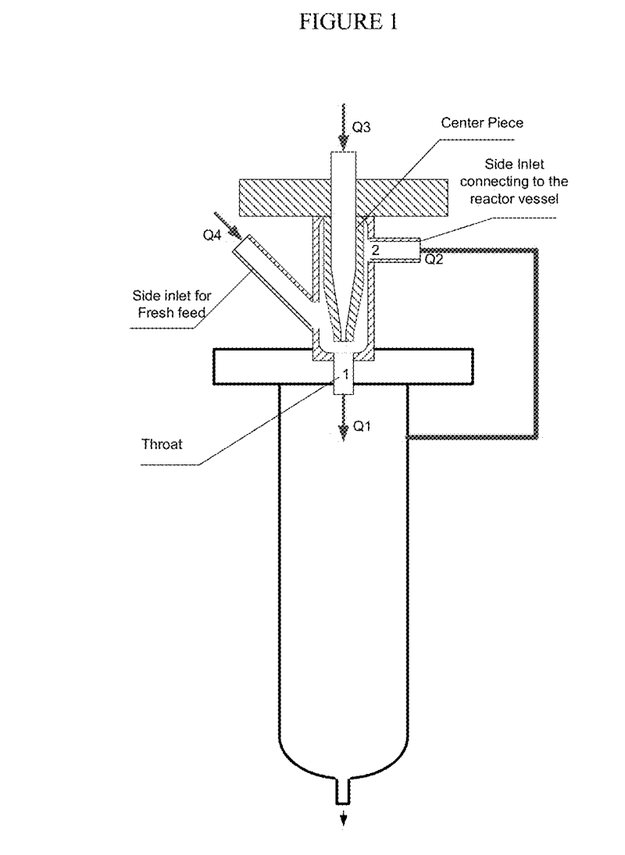
FIG. 1 is an overview of a Venturi nozzle reactor.

Another advantage to positioning the introduction location of the hydrocarbon feed stream close to the orifice of the nozzle is that it can improve the quality of the alkylate gasoline blending components. In one embodiment, it increases the production of C8 hydrocarbons, and gives an alkylate gasoline blending component with a high RON. RON refers to Research-Method Octane Number. The Research-Method Octane Number (RON) is determined using ASTM D 2699-07a. In one embodiment the alkylate gasoline blending component has a RON greater than 85, greater than 90, greater than 93.3, 94 or higher, greater than 95, or greater than 98. In some embodiments the alkylate gasoline blend components have a low Reid Vapor Pressure. The alkylate blend components can have a Reid Vapor Pressure of 7.0 psi (4.827e+004 newtons/square meter) or less. In one embodiment the gasoline blending components have a Reid Vapor Pressure (RVP) less than 4.0 psi (2.758e+004 newtons/square meter). In other embodiments the gasoline blending components have a RVP of 2.8 psi (1.931e+004 newtons/square meter) or less, or less than the amount defined by the equation: RVP=−0.035×(50 vol % boiling point, ° C.)+5.8, in psi. The chart of this equation is shown in FIG. 1 in US Patent Publication Number US 20100025292.

The introducing of the hydrocarbon feed stream can be done at a single location or at multiple locations. These different embodiments are illustrated in the figures. The choice of number of introducing locations can depend on the size of the nozzle and the amount and effectiveness of mixing that is needed. The hydrocarbon feed stream can be introduced in any location in the nozzle that is close to the orifice. For example, the hydrocarbon feed stream can be introduced at a location selected from the group of before the orifice of the nozzle, in a chamber in the nozzle between the orifice and the throat, in the throat of the nozzle, and combinations thereof.

The catalyst is one that is useful for alkylation. In one embodiment the catalyst is an acidic liquid catalyst. Examples of acidic liquid catalysts are ionic liquid catalysts.

An acidic ionic liquid catalyst is composed of at least two components which form a complex. The acidic ionic liquid catalyst comprises a first component and a second component. The first component of the acidic ionic liquid catalyst can comprise a Lewis Acid selected from components such as Lewis Acidic compounds of Group 13 metals, including aluminum halides, alkyl aluminum halide, gallium halide, and alkyl gallium halide (see International Union of Pure and Applied Chemistry (IUPAC), version3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the acidic ionic liquid catalyst.

The second component making up the acidic ionic liquid catalyst is an organic salt or mixture of salts. These salts can be characterized by the general formula Q+A−, wherein Q+ is an ammonium, phosphonium, boronium, iodonium, or sulfonium cation and A− is a negatively charged ion such as Cl−, Br−, ClO$_4^-$, NO$_3^-$, BF$_4^-$, BCl$_4^-$, PF$_6^-$, SbF$_6^-$, AlCl$_4^-$, TaF$_6^-$, CuCl$_2^-$, FeCl$_3^-$, HSO$_3^-$, RSO$_3^-$, SO$_3$CF$_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same. In one embodiment the acidic ionic liquid catalyst is N-butylpyridinium chloroaluminate.

In another embodiment the acidic ionic liquid catalyst can have the general formula $RR'R''NH^+Al_2CL_7^-$, wherein N is a nitrogen containing group, and wherein R, R', and R'' are alkyl groups containing 1 to 12 carbons, and where R, R', and R'' may or may not be the same.

The presence of the first component should give the acidic ionic liquid a Lewis or Franklin acidic character. Generally, the greater the mole ratio of the first component to the second component, the greater is the acidity of the acidic ionic liquid catalyst.

In one embodiment, the acidic ionic liquid catalyst is mixed in either a reactor or in the nozzle with a hydrogen halide or an organic halide. The hydrogen halide or organic halide can boost the overall acidity and change the selectivity of the acidic ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, iospentyl halides, isobutyl halides, butyl halides, propyl halides and ethyl halides. Other alkyl chlorides or halides having from 1 to 8 carbon atoms can be also used. The alkyl halides can be used alone or in combination. The use of alkyl halides to promote hydrocarbon conversion by acidic ionic liquid catalysts is taught in U.S. Pat. No. 7,495,144 and in U.S. patent application Ser. No. 12/468,750, filed May 19, 2009.

It is believed that the alkyl halide decomposes under hydroconversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is the same as a halide component of the acidic ionic liquid catalyst. In one embodiment the alkyl halide is an alkyl chloride, for example t-butyl chloride. A hydrogen chloride or an alkyl chloride can be used advantageously, for example, when the acidic ionic liquid catalyst is a chloroaluminate.

The process unit for the production of alkylate gasoline comprises a nozzle with a conduit for introducing the hydrocarbon feed stream to an orifice in the nozzle at a distance from the orifice that is close to the orifice. The orifice in the nozzle dispenses one or more recirculated streams comprising ionic liquid catalyst into a chamber in the nozzle. A throat connects the chamber in the nozzle to an alkylation zone where alkylate gasoline blending components are produced.

In one embodiment the process unit additionally comprises an inlet that feeds an internal recirculated stream from the alkylation zone to the chamber of the nozzle. This embodiment is shown in the figures.

As described previously, the alkylate gasoline blending components produced in the process unit can have a reduced level of C11+ hydrocarbons. In one embodiment the flow of the hydrocarbon feed stream through the conduit is at an angle, from a direction of flow of the one or more recirculated streams toward the orifice, that is selected to provide improved reaction conditions for making alkylate gasoline blending components. For example, the flow of the hydrocarbon feed stream through the conduit is at an angle from 0 degrees to 90 degrees from a direction of flow of the one or more recirculated streams towards the orifice.

The following is a description of embodiments of the process with reference to the figures:

FIG. 1. A fresh hydrocarbon feed stream (Q4) containing both olefin and isoparaffin feeds was introduced into a nozzle loop reactor at an angle of about 45° from a direction of the flow of a main recirculation stream (Q3) towards an orifice. The fresh hydrocarbon feed stream was introduced in a chamber of the nozzle housing a center piece of the nozzle from which a recirculation stream, named external recirculation stream, (Q3) flows in. Another recirculated reactant stream (Q2), named internal recirculation stream, from an alkylation zone that is a reactor vessel containing an ionic liquid catalyst is also fed via an inlet on the side of the nozzle (2) to the chamber of the nozzle. The orifice dispenses the external recirculation stream at high speed into the chamber, where it mixes with the hydrocarbon feed stream and the internal recirculation stream. A mixture (Q1) of the external recirculation stream (Q3), the hydrocarbon feed stream (Q4), and the internal recirculation stream (Q2) are dispensed through a throat (1) of the nozzle into the alkylation reactor vessel. Alkylate products are produced and eluted from the alkylation reactor vessel.

Figure 2A:
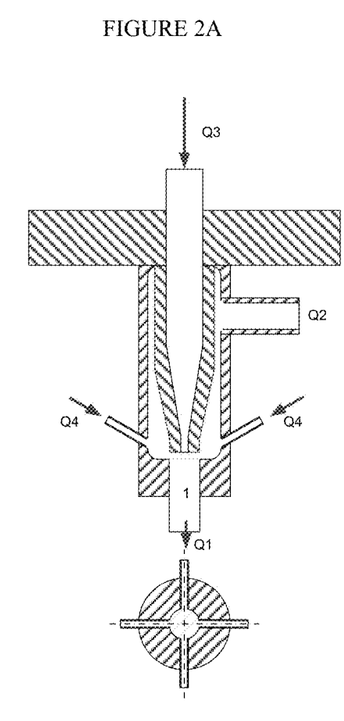
FIG. 2a is a Venturi nozzle with multiple side inlets for fresh hydrocarbon feed, where fresh hydrocarbon feed injects to the internal chamber in the nozzle.

FIG. 2A shows an embodiment of a Venturi nozzle loop reactor where the fresh hydrocarbon feed (Q4) is introduced in four locations on opposing sides of a nozzle loop reactor at an angle of approximately 60° from a direction of the flow of a recirculated reactant stream (Q3) towards an orifice. The hydrocarbon feed streams are introduced in a chamber of the nozzle housing a center piece of the nozzle from which an external recirculation stream flows in.

Figure 2B:
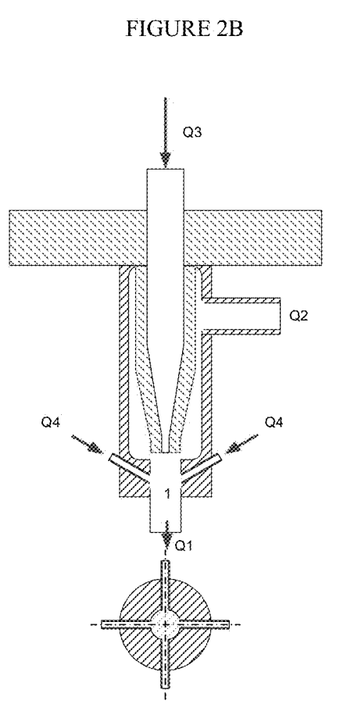
FIG. 2b is a Venturi nozzle with multiple side inlets for fresh hydrocarbon feed, where fresh hydrocarbon feed injects to the throat of the nozzle.

FIG. 2B is similar to FIG. 2A, with the location of the introduction of the four hydrocarbon feed streams moved to the throat of the nozzle. In this embodiment, the hydrocarbon feed streams are introduced from the side of the throat and below the center piece from which an external recirculation stream flows in.

Figure 3:
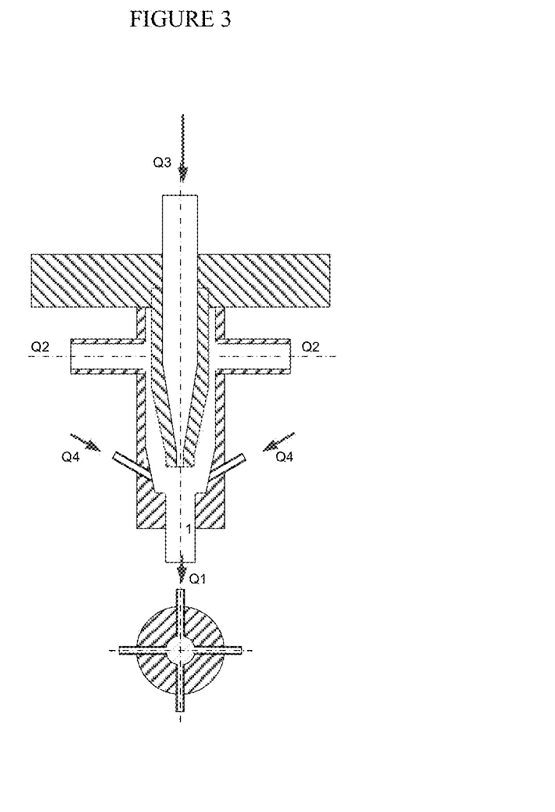
FIG. 3 is a Venturi nozzle with multiple side inlets connecting to the reactor vessel feeding internal recirculated streams to the nozzle, and multiple side inlets for fresh hydrocarbon feed.

FIG. 3 is similar to FIG. 2A, with multiple side inlets delivering recirculated reactant streams (Q2) into the nozzle.

Figure 4:
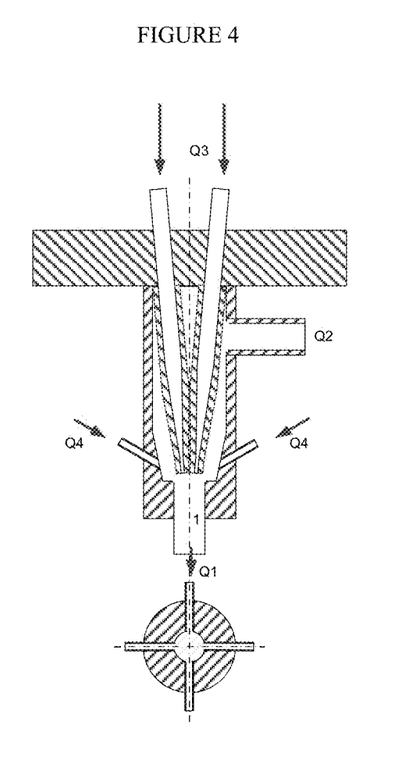
FIG. 4 is a Venturi nozzle with multiple center pieces feeding external recirculated streams to the orifice in the nozzle and multiple side inlets for fresh hydrocarbon feed.

FIG. 4 shows a Venturi nozzle loop reactor with multiple center pieces to the nozzle each having an orifice dispensing an external recirculation stream into a chamber in the nozzle.

The fresh hydrocarbon feeds (Q4) were introduced in multiple locations into the nozzle loop reactor at an angle of approximately 50° from the direction of the flows of the multiple external recirculation streams (Q3) towards the orifices. As in the earlier figures, a recirculated reactant stream (Q2) from an alkylation zone that is an alkylation reactor vessel was also fed via an inlet on the side of the nozzle to the chamber in the nozzle. The orifices dispensed the external recirculation streams at high speed into the chamber, where they mixed with the hydrocarbon feed streams and the recirculated reactant stream. A mixture (Q1) of the external recirculation streams (Q3), the hydrocarbon feed streams (Q4), and the internal recirculation stream (Q2) were dispensed through a throat (1) of the nozzle into the alkylation reactor vessel.

Figure 5:
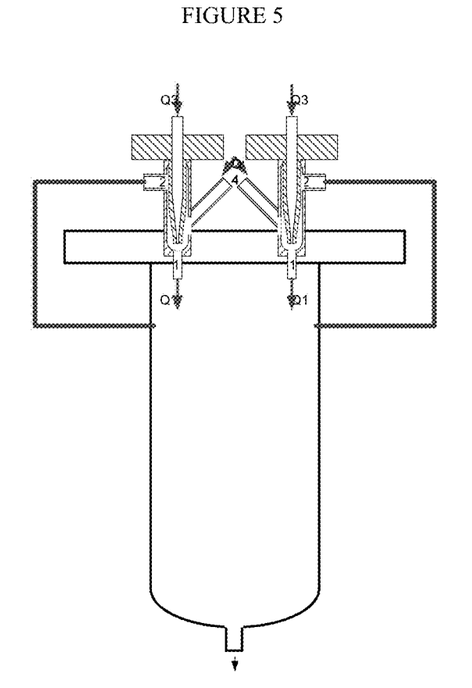
FIG. 5 is a Venturi nozzle reactor with multiple Venturi nozzles, each with their own internal recirculated stream.

FIG. 5 shows a process unit with multiple Venturi nozzles, similar to those described in FIG. 1, dispensing into the same alkylation zone. Each Venturi nozzle has its own recirculated reactant stream coming from the same alkylation zone FIG. 6A is similar to FIG. 2A, with the location of the introduction of the four hydrocarbon feed streams still in the chamber of the nozzle, but in between the orifice and the throat of the nozzle. In this embodiment, the hydrocarbon feed streams are introduced very close to the tip of the center piece where the external recirculation stream is fed in.

FIG. 6B shows a Venturi nozzle loop reactor where the hydrocarbon feed stream (Q4) is introduced through a dip tube into the center piece of the nozzle (rather than into the chamber or the throat of the nozzle) such that the hydrocarbon feed stream is introduced close to the orifice of the nozzle. The hydrocarbon feed stream is introduced at an angle of 0 degrees from the direction of the flow of the external recirculation feed stream towards the orifice. The other features of the process unit are as described in FIG. 1.

The term "comprising" means including the elements or steps that are identified following that term, but any such elements or steps are not exhaustive, and an embodiment may include other elements or steps. For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

EXAMPLES

Example 1

A process unit was tested in a laboratory. The process unit was a Venturi nozzle loop reactor configured as shown in FIG. 6B. In one configuration of the process unit, the hydrocarbon feed stream was introduced via a conduit into a nozzle through which an external recirculation stream flows towards an orifice in the nozzle. The two streams started mixing about 5 inches (12.7 cm) away from the orifice of the nozzle. In a second configuration, the hydrocarbon feed stream was introduced through a dip tube in the conduit through which an external recirculation stream flowed towards an orifice in the nozzle into the same nozzle loop reactor operated at the same process conditions. The two streams start mixing about 0.5 inch (1.27 cm) from the orifice of the nozzle. In both configurations the hydrocarbon feed stream was introduced at an angle of 0 degrees from the direction of the flow of the external recirculation stream towards the orifice.

The external recirculated stream (Q3), the hydrocarbon feed stream (Q4) comprised of olefin and isoparaffin, and an internal recirculated stream (Q2) comprised of primarily isoparaffins from an alkylation reactor and catalyst were fed into a chamber in the nozzle. The mixture of the isoparaffin feed stream, the olefin feed stream, and the recirculated reactant streams was dispensed into the alkylation reactor through a throat of the nozzle.

The alkylation reactor comprised N-butylpyridinium chloroaluminate ($C_5H_5C_4H_9Al_2Cl_7$) ionic liquid catalyst that had the following elemental composition.

TABLE I

| | |
|---|---|
| Wt % Al | 12.4 |
| Wt % Cl | 56.5 |
| Wt % C | 24.6 |
| Wt % H | 3.2 |
| Wt % N | 3.3 |

The alkylate product distributions from the alkylation reactor from the process unit operated in the two configurations are shown in Table II.

TABLE II

Effect of Position of Olefin Feed Stream on Alkylate Gasoline Properties

| Distance From Introduction of Hydrocarbon Feed Stream to Nozzle Orifice | 12.7 cm (5 inches) | 1.27 cm (0.5 inch) |
|---|---|---|
| C5 (Wt %) | 4-5 | 5 |
| C6 (Wt %) | 8-10 | 6 |
| C7 (Wt %) | 8-9 | 8 |
| C8 (Wt %) | 55-57 | 66.2 |
| C9 (Wt %) | 12-14 | 9.5 |
| C10 (Wt %) | 3-4 | 2.5 |
| C11+ (Wt %) | 6-8 | 3.2 |
| TMP/C8 | 80-81 | 82 |
| RON | 94 | 94 |

By reducing the distance from the introduction of the hydrocarbon feed stream to the nozzle orifice the selectivity to C8 was increased by about 10%. The amount of less valuable C11+ was decreased substantially, by as much as 60%. The improvement in the alkylate gasoline quality was done with no significant changes to the process unit other than changing where the olefin feed stream was introduced to the nozzle.

Example 2

A process unit having a Venturi nozzle was tested in a pilot plant. The process unit had a ½" feed pipe for the hydrocarbon feed at an angle of 60° from the direction of the flow of an external recirculation stream towards the orifice. The hydrocarbon feed was introduced to the Venturi nozzle through (1) the ½" feed pipe and (2) a ¼" dip tube inserted in the pipe. The effluent end of the dip tube was placed directly adjacent to the nozzle orifice, within 1 times the diameter of the orifice. The nozzle dispensed a mixture of external recirculated ionic liquid catalyst, internal recirculated ionic liquid catalyst and unreacted isoparaffin, and a fresh hydrocarbon feed stream comprising isobutane and butene into an alkylation reactor. By feeding the hydrocarbon feed stream through the dip tube the linear velocity of the hydrocarbon feed through the conduit into the nozzle was increased from 0.6 m/s to 7.7 m/s. The placement of the dip tube significantly reduced the residence time of the hydrocarbon feed in a zone of the Venturi nozzle with insufficient mixing. This reduced the amount of C11+ products produced, and increased the RON of the alkylate gasoline blending components produced by the alkylation reactor.

What is claimed is:

1. A process unit for production of alkylate gasoline, comprising:
   a) a nozzle having an orifice that dispenses one or more recirculated streams comprising an ionic liquid catalyst into a chamber in the nozzle, wherein the chamber of the nozzle houses a center piece from which one or more external recirculated streams flow towards the orifice; and wherein the center piece is in the center of the nozzle;
   b) a dip tube, inserted into the center piece and within a flow of the one or more external recirculated streams, for introducing a hydrocarbon feed stream comprising an olefin to the orifice at a distance from the orifice that is within 25 times a diameter of the orifice;
   c) a throat connecting the chamber in the nozzle to an alkylation zone where alkylate gasoline blending components are produced; and
   d) an inlet on the side of the nozzle that feeds an internal recirculated stream from the alkylation zone to the chamber of the nozzle.

2. The process unit of claim 1, wherein the distance from the orifice is within 10 times the diameter of the orifice.

3. The process unit of claim 2, wherein the distance from the orifice is from 1 times the diameter of the orifice.

4. The process unit of claim 2, wherein the distance from the orifice is from zero to 5 times the diameter of the orifice.

5. The process unit of claim 1, wherein a flow of the hydrocarbon feed stream through the dip tube is at an angle of 0 degrees from a direction of flow of the one or more external recirculated streams towards the orifice.

6. The process unit of claim 1, wherein there are multiple inlets.

7. The process unit of claim 6, wherein the multiple inlets are on the side of the nozzle.

8. The process unit of claim 1, wherein the nozzle is a Venturi.

9. The process unit of claim 1, wherein the dip tube increases a linear velocity of the hydrocarbon feed through the nozzle.

10. The process unit of claim 9, wherein the linear velocity is increased from 0.6 to 7.7 m/s.

11. The process unit of claim 1, wherein the dip tube is narrower than the center piece.

12. A process unit for production of alkylate gasoline, comprising:
   a) a nozzle having an orifice that dispenses one or more recirculated streams comprising an ionic liquid catalyst into a chamber in the nozzle, wherein the chamber of the nozzle houses a center piece from which one or more external recirculated streams from a reaction zone flow towards the orifice; and wherein the center piece is in the center of the nozzle;
   b) a feed pipe, on a side of the nozzle, having a dip tube inserted into the feed pipe, wherein the feed pipe and the dip tube inserted in the feed pipe are used for introducing a hydrocarbon feed stream comprising an olefin to the orifice at a distance from the orifice that is within 25 times a diameter of the orifice; wherein the dip tube increases a linear velocity of the hydrocarbon feed through the feed pipe; and
   c) a throat connecting the chamber in the nozzle to an alkylation zone where alkylate gasoline blending components are produced.

13. The process unit of claim 12, wherein the linear velocity is increased from 0.6 to 7.7 m/s.

* * * * *